United States Patent [19]

Agematu et al.

[11] Patent Number: 5,232,943
[45] Date of Patent: Aug. 3, 1993

[54] ANTIBIOTICS MER-AF1032A AND MER-AF1032B

[75] Inventors: Hitosi Agematu, Hadano; Yoshio Watanabe, Fujisawa; Hiroyuki Chiba, Yamato; Rei Kaneto, Yokohama; Norio Shibamoto, Chigasaki; Takeo Yoshioka, Ayase; Toshihiko Kumamoto, Fujisawa; Hiroshi Nishida, Yokosuka; Rokuro Okamoto, Fujisawa, all of Japan

[73] Assignee: Mercian Corporation, Tokyo, Japan

[21] Appl. No.: 885,771

[22] Filed: May 20, 1992

[30] Foreign Application Priority Data

May 22, 1991 [JP] Japan .................................. 3-145222
Feb. 10, 1992 [JP] Japan .................................. 4-23972

[51] Int. Cl.⁵ ...................... A61K 31/35; C07D 311/92
[52] U.S. Cl. ...................................... 514/455; 549/389
[58] Field of Search .......................... 549/389; 514/455

[56] References Cited

FOREIGN PATENT DOCUMENTS 0412160 2/1991 European Pat. Off. .

Primary Examiner—Nicky Chan
Attorney, Agent, or Firm—Cushman, Darby & Cushman

[57] ABSTRACT

Antibiotic Mer-AF1032A represented by the following formula (I) and its isomer antibiotic Mer-AF1032B are disclosed. Also disclosed are a method for preparing the antibiotics comprising the cultivation of a strain belonging to genus Penicillium and a pharmaceutical composition comprising one of these antibiotics and useful as an antifungal agent.

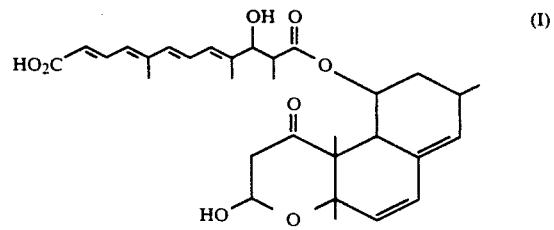

3 Claims, 8 Drawing Sheets

ANTIBIOTICS MER-AF1032A AND MER-AF1032B

BACKGROUND OF THE INVENTION

1. Field of the Invention

The present invention relates to novel antibiotics Mer-AF1032A and Mer-AF1032B, and a method for preparing the same.

2. Description of the Related Art

About 20 types of antifungal substances are known including polyene-type compounds such as Amphotericin B, nystatin, and trichomycin; imidazole-type compounds such as miconazole and ketoconazole; and flucytosine. However, these substances are not fully satisfactory from the standpoint of their toxicity and efficacy. Furthermore, since it has been recognized that only limited lowering of toxicity and enhancement of efficacy can be realized through chemical modification of known antifungal substances, the development of a novel type of antifungal substance has been desired.

SUMMARY OF THE INVENTION

Accordingly, an object of the present invention is to provide a novel antifungal substance and a process for preparation thereof Another object of the present invention is to provide a pharmaceutical composition comprising an effective amount of the antifungal substance, and a method for treating fungal infections comprising the step of administering the antifungal substance or the pharmaceutical composition comprising the antifungal substance to a patient.

The inventors of the present invention separated strains of microorganisms from various soil sources and screened metabolites produced by the strains. As a result, they found that a strain belonging to the genus Penicillium produces substances in a cultured medium that exhibit antimicrobial activity against *Candida albicans*. By successively separating and purifying the substances and examining their physicochemical properties, the inventors confirmed that the substances have physicochemical properties distinct from those of any known substance and that they have excellent antifungal activity. The present invention was achieved on the basis of this finding.

Thus, the present invention provides novel antibiotics Mer-AF1032A and Mer-AF1032B, and a process for preparing these antibiotics. In accordance with other of its features, the present invention provides a pharmaceutical composition comprising an effective amount of a substance selected from the group consisting of the antibiotics Mer-AF1032A and Mer-AF1032B which is useful for the treatment of fungal infection. Further objects, features and advantages of the present invention will become apparent from the Description of the Preferred Embodiments which follows, when read in light of the accompanying Examples.

DETAILED DESCRIPTION OF THE PREFERRED EMBODIMENTS

The antibiotic Mer-AF1032A is represented by the following formula:

and its physicochemical properties are as follows:

(1) Color and Appearance: pale yellow powder;

(2) Molecular Formula : $C_{31}H_{40}O_8$;

(3) Mass Spectrum (FAB-MS, Matrix; 2,2'-dithiodiethanol); Positive: 563[(M+Na)$^+$], 540[M$^+$], 523[(M+H−H$_2$O)$^+$]. Negative: 539[(M−H)$^-$].

(4) Melting Point: 123°-126° C.

(5) Specific Rotation: $[\alpha]_D^{23}$+58.6° (c 0.4, chloroform).

Figure 1:
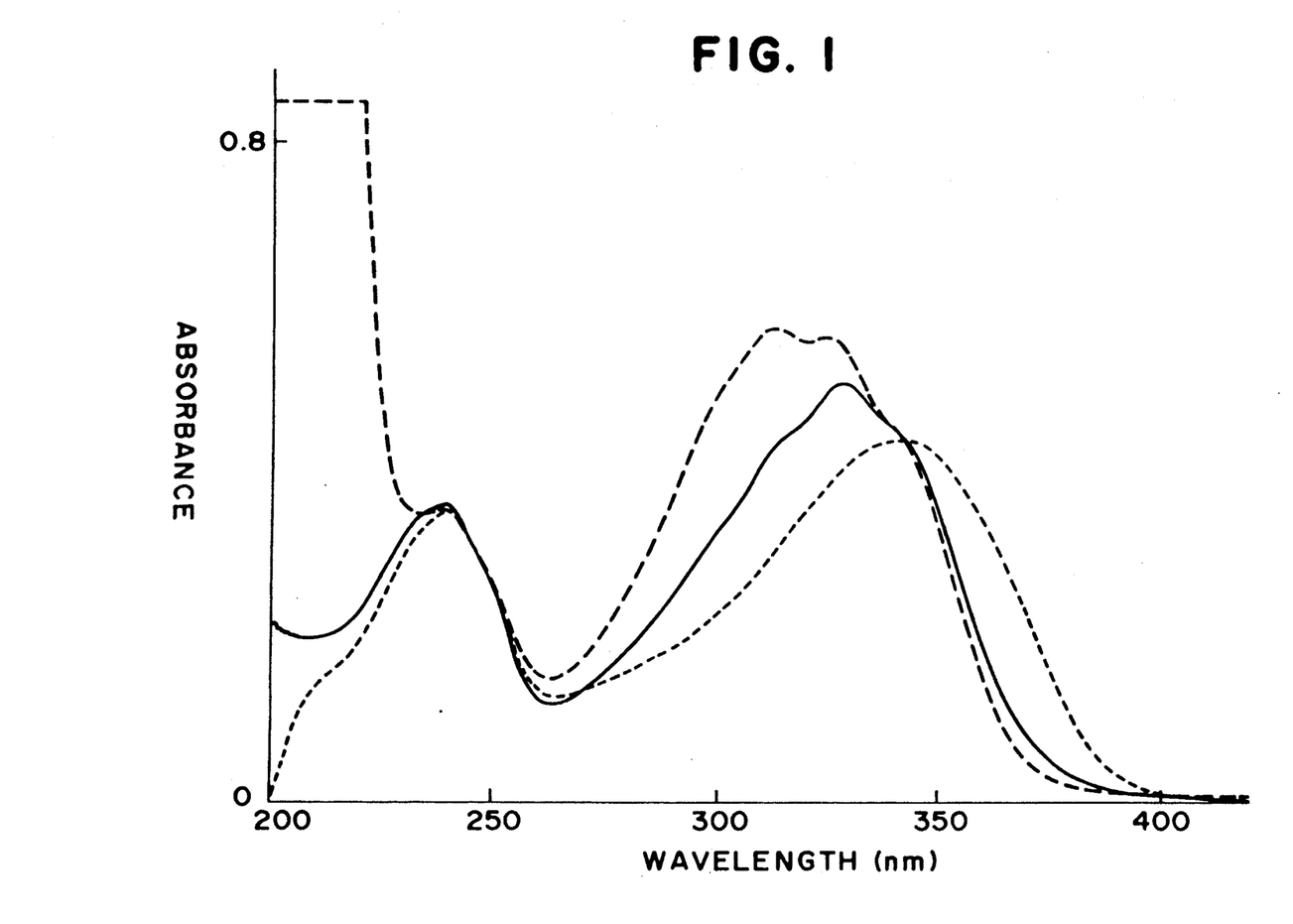
FIG. 1 shows the ultraviolet absorption spectra of the antibiotic Mer-AF1032A, in which —represents the spectrum measured in methanol; ---- represents the spectrum measured in acidic methanol; and - - - represents the spectrum measured in basic methanol.
Figure 3:
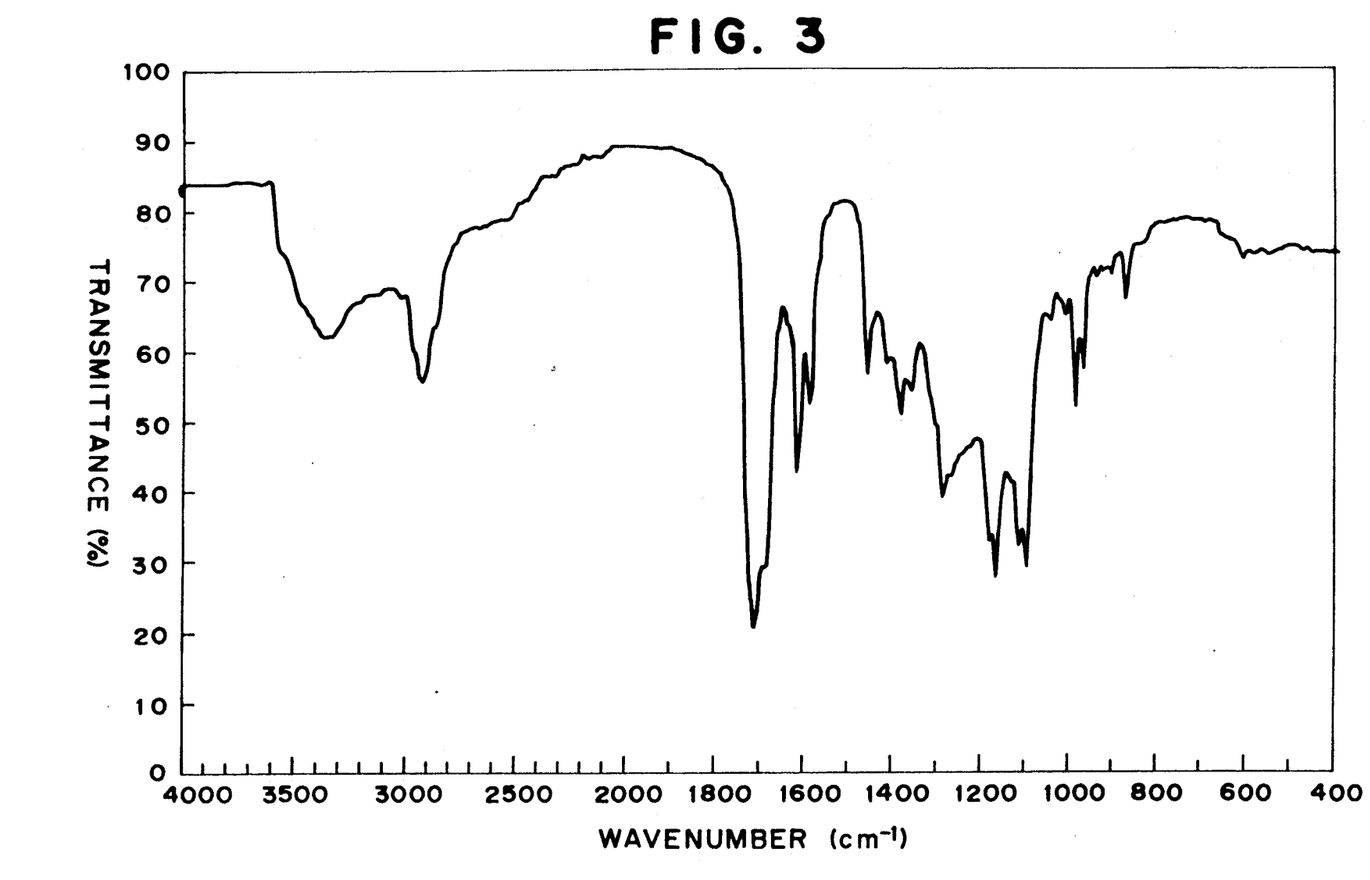
FIG. 3 shows the infrared absorption spectrum of the antibiotic Mer-AF1032A measured in chloroform.

(6) Ultra-Violet Absorption Spectrum: as shown in FIG. 1; λ max nm (ε): methanol: 338.6(sh,21400), 328.0(23800), 315.4(sh,20800), 239.2(16900); acidic methanol: 340.0(20600), 239.8(16500); and basic methanol: 338.6(sh,21400), 324.2(26300), 312. 2(26900), 238.8(16600);

(7) Infrared Absorption Spectrum: as shown in FIG. 3 (measured in chloroform); (cm$^{-1}$): 3350(br), 2920, 1710, 1685, 1610, 1580, 1450, 1410, 1380, 1355, 1280, 1180, 1160, 1110, 1095, 980, 960, 865;

(8) Solubility: soluble in chloroform, ethyl acetate, and methanol at a concentration of more than 1 mg/ml; soluble in toluene at a concentration of not more than 1 mg/ml; and substantially insoluble in water;

(9) Color Reaction: positive by phosphomolybdic acid reagent, vanillin-phosphoric acid reagent, and 2,4-dinitrophenylhydrazine reagent; and negative in Dragendorff's reagent, ninhydrin reagent, Rydon-Smith reagent, and ferric chloride.

Figure 5:
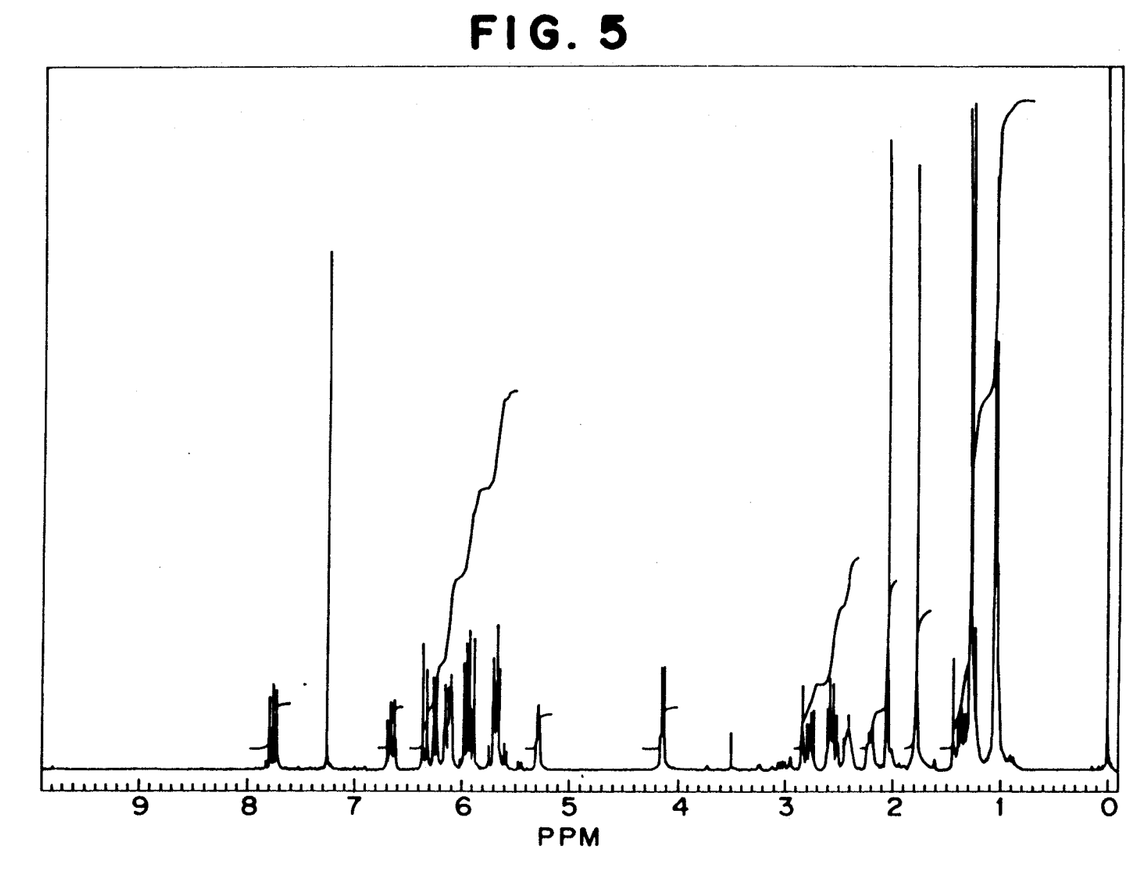
FIG. 5 shows the 400 MHz $^1$H NMR spectrum of the antibiotic Mer-AF1032A measured in CDCl$_3$.
Figure 7:
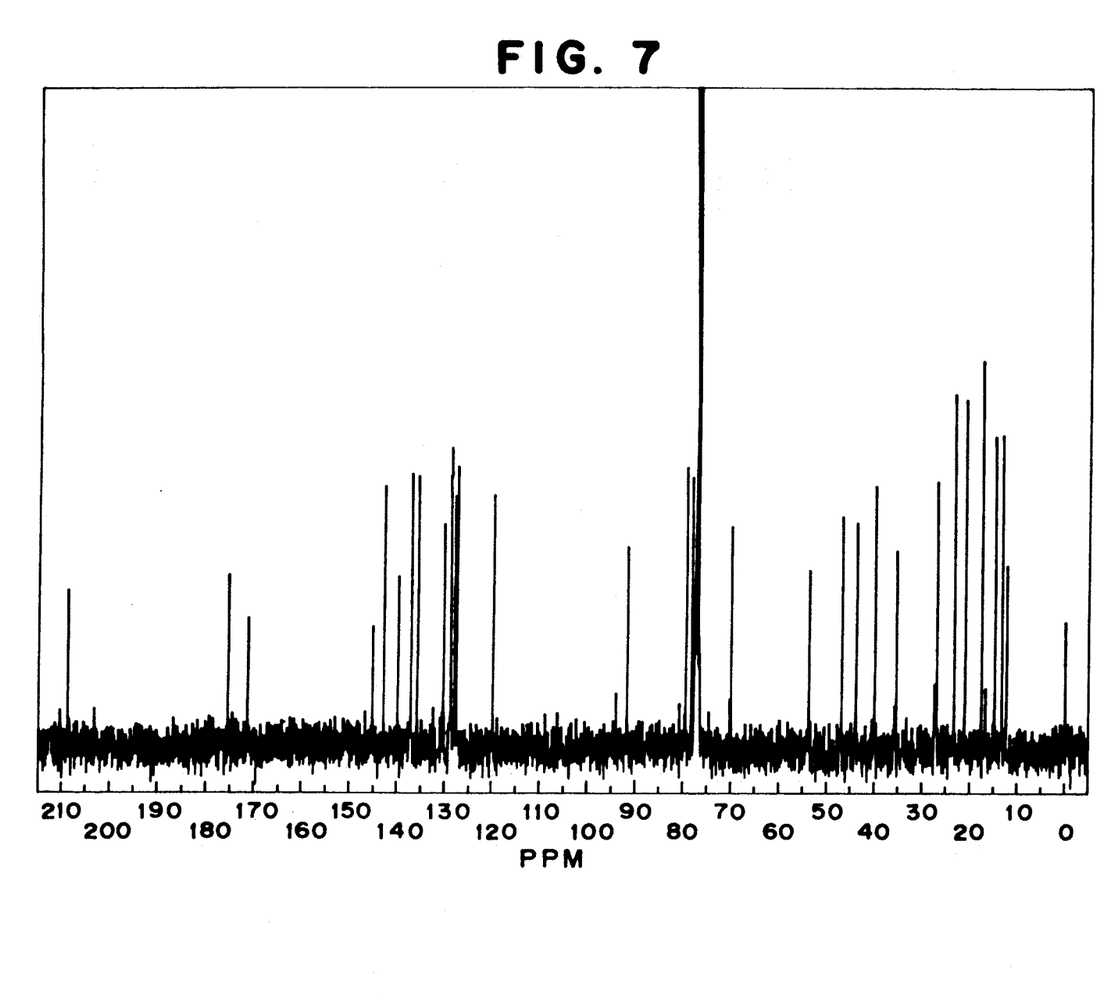
FIG. 7 shows the 100 MHz $^{13}$C NMR spectrum of the antibiotic Mer-AF1032A measured in CDCl$_3$.

(10) Rf Value on a Thin Layer Chromatogram (Merck, silicagel plate F-254): 0.38 (chloroform: methanol =7:1) and 0.45 (toluene:ethyl acetate:acetic acid =40:50:1);

(11) $^1$H-NMR Spectrum: as shown in FIG. 5 (measured in CDCl$_3$): δ TMS(ppm): 1.04(3H,d,J=6 6), 1.06(3H,d,J=6.6), 1.26(3H,s), 1.28(3H,s), 1.35(1H,t,J=12.5), 1.78(3H,s), 2.05(3H,s), 2.20(1H,m), 2.40(1H,m), 2.53(1H,dd,J=13.9,4.0), 2.58(1H,quintet like,J=7.3), 2.76(1H,dd,J=13.9,8.4), 2.83(1H,br d,J=2.6), 4.13(1H,d,J=8.1), 5.28(1H,dd,J=8.1,4.0), 5.67(1H,d,J=9.9), 5.70(1H,br s), 5.90(1H,d, J=15.0), 5.96(1H,d,J=9.9), 6.10(1H,br s), 6.13(H,d,J=11.0), 6.24(1H,d,J=12.1), 6.33(1H,d,J=15.0), 6.65(1H,dd,J=15.0,11.0), 7.76(1H,dd.J=15.0,12.1): (12) $^{13}$C-NMR Spectrum: as shown in FIG. 7 (measured in CDCl$_3$ and the data relating to the multiplicity of the signals were obtained by DEPT experiment): δ TMS(ppm): 208.6s, 175.3s, 171.2s, 145.0s, 142.4d, 139.8s, 137.0d, 135.8d, 130.3d, 130.0s, 128.9d, 128.7d, 128.0d, 127.5d, 119.6d,91. 7d, 79.3d, 78.2s, 70.0d, 53.7s, 46.9t, 43.8d, 39.9d, 35.4t, 27.0d, 23.2q, 20.9q, 17.6q, 14.9q, 13.2q, 12.4q; and (13) Classification by neutral, acidic, or basic property: weakly acidic, on a silica gel thin layer plate with a pH indicator.

The antibiotic Mer-AF1032B is represented by the following formula:

and its physicochemical properties are as follows:

(1) Color and Appearance: pale yellow powder;

(2) Molecular Formula: $C_{31}H_{40}O_8$;

(3) Mass Spectrum (FAB-MS, Matrix; 2,2'-dithiodiethanol); Positive: 563[(M+Na)$^+$], 540[M$^+$], 523[(M+H−H$_2$O)$^+$]. Negative: 539[(M−H)$^-$].

(4) Melting Point: 126°–129° C.

(5) Specific Rotation: [α]$_D^{26}$+57.3° (c 0.075, chloroform).

Figure 2:
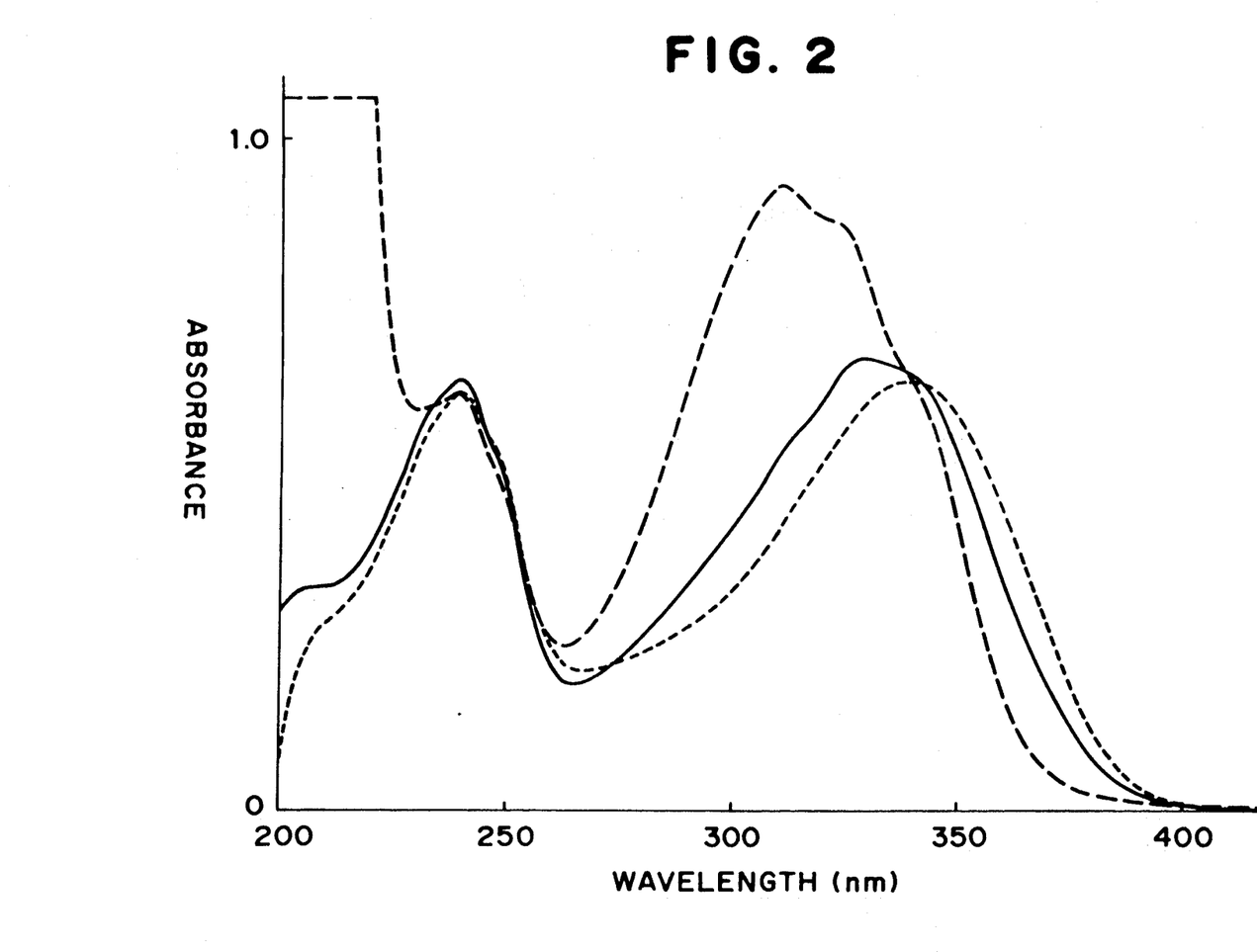
FIG. 2 shows the ultraviolet absorption spectra of the antibiotic Mer-AF1032B, in which —represents the spectrum measured in methanol; ---- represents the spectrum measured in acidic methanol; and - - - represents the spectrum measured in basic methanol.
Figure 4:
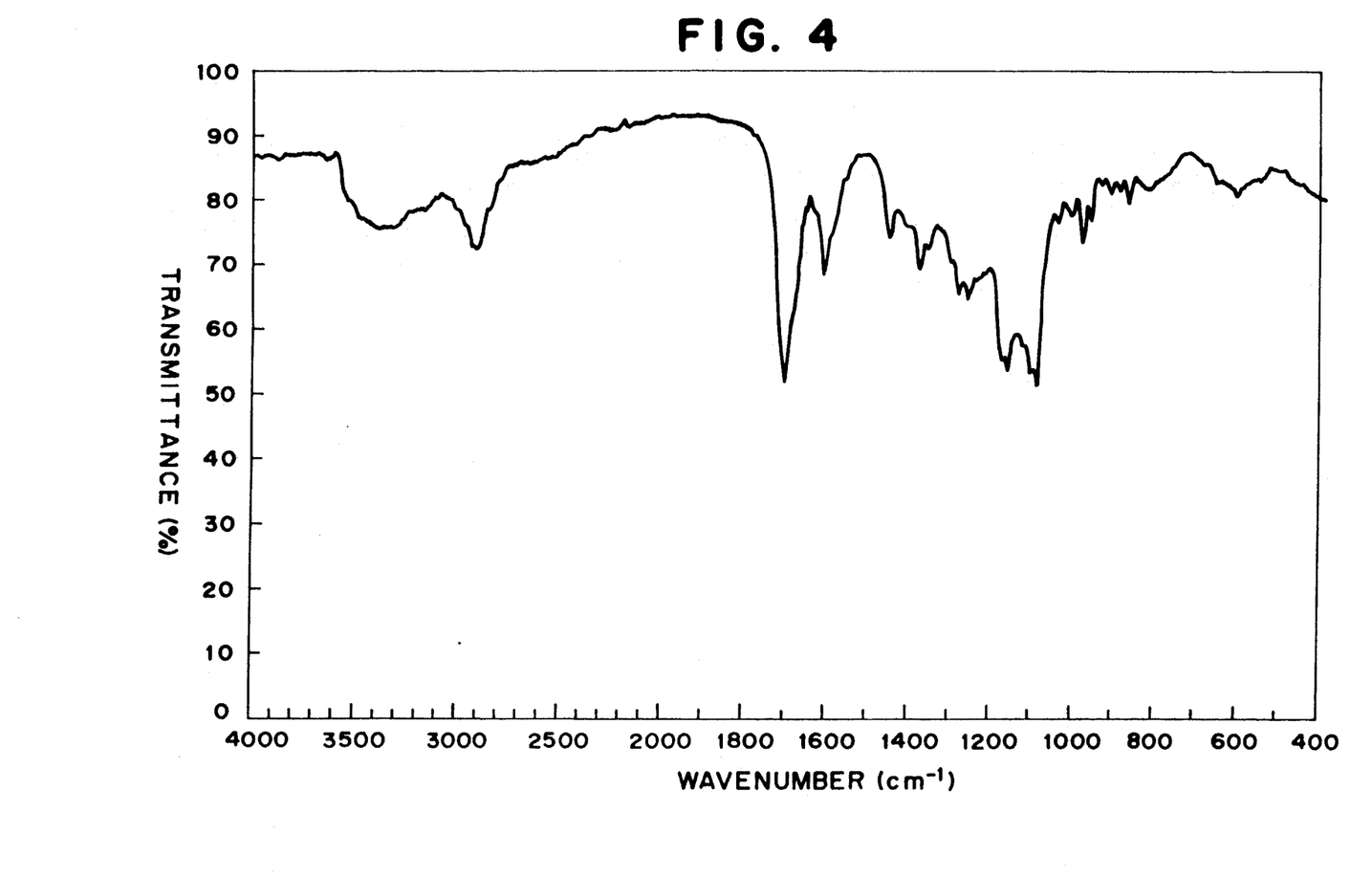
FIG. 4 shows the infrared absorption spectrum of the antibiotic Mer-AF1032B measured in chloroform.

(6) Ultra-Violet Absorption Spectrum: as shown in FIG. 2; λ max nm (ε): methanol: 338.8(sh,18800), 329.6(19400), 240.0(18600); acidic methanol: 338.6(18400), 240.0(18000); and basic methanol: 338.8(sh,18600), 321.8(25400), 311.0(26900), 239.2(17900);

(7) Infrared Absorption Spectrum: as shown in FIG. 4 (measured in chloroform); (cm$^{-1}$): 3375(br), 2900, 1700, 1605, 1445, 1400, 1375, 1350, 1300, 1280, 1255, 1170, 1160, 1110, 1100, 1085, 975, 860;

(8) Solubility: soluble in chloroform, ethyl acetate, and methanol at a concentration of more than 1 mg/ml; soluble in toluene at a concentration of not more than 1 mg/ml; and substantially insoluble in water;

(9) Color Reaction: positive by phosphomolybdic acid reagent, vanillin-phosphoric acid reagent, and 2,4-dinitrophenylhydrazine reagent; and negative in Dragendorff's reagent, ninhydrin reagent, Rydon-Smith reagent, and ferric chloride.

Figure 6:
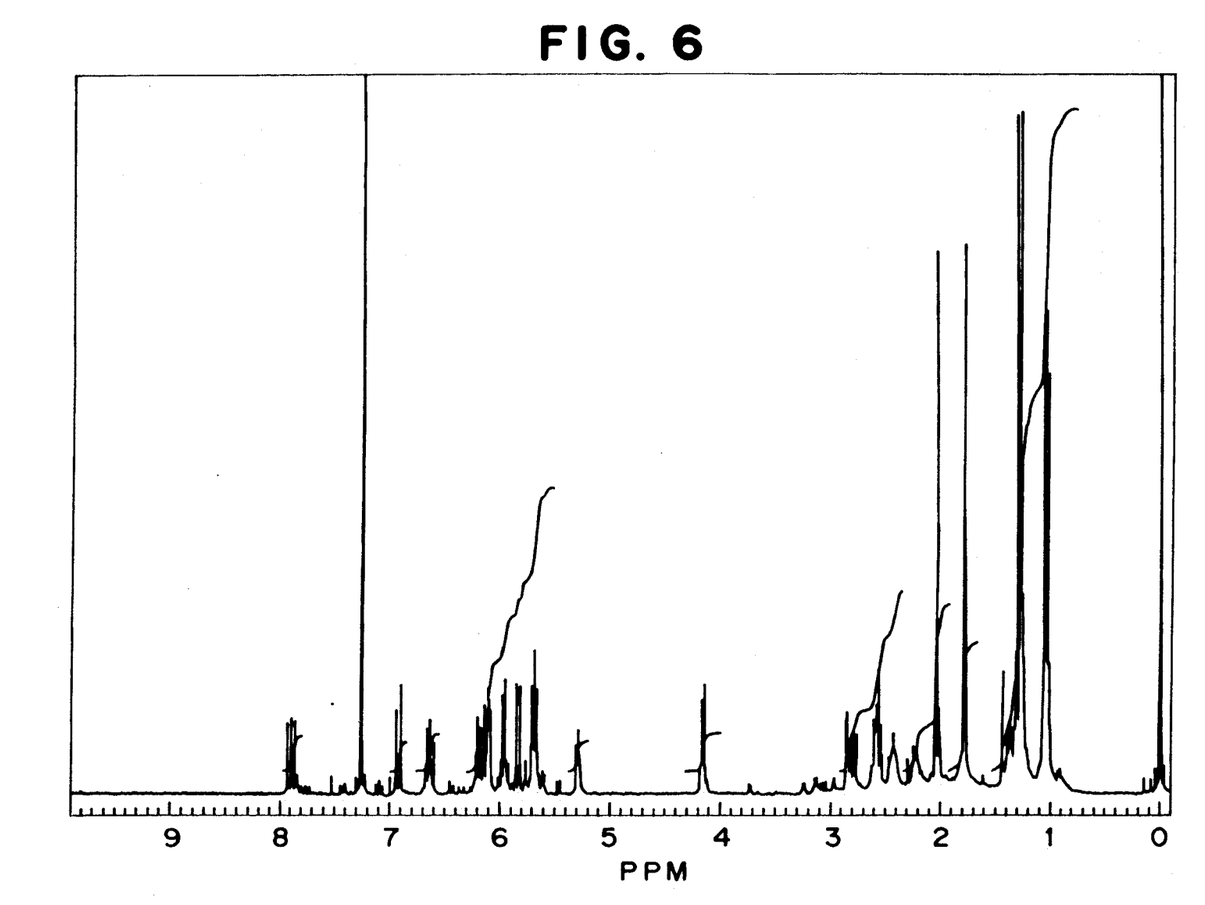
FIG. 6 shows the 400 MHz $^1$H NMR spectrum of the antibiotic Mer-AF1032B measured in CDCl$_3$.

(10) Rf Value on a Thin Layer Chromatogram (Merck, silicagel plate F-254): 0.38 (chloroform: methanol=7:1) and 0.45 (toluene:ethyl acetate:acetic acid=40:50:1);

(11) $^1$H-NMR Spectrum: as shown in FIG. 6 (measured in CDCl$_3$): δ TMS(ppm): 1.03(3H,d,J=7.0), 1.06(3H,d,J=7.3), 1.27(3H,s), 1.31(3H,s), 1.36(1H,br t,J=13.2), 1 79(3H,s), 2.04(3H,s), 2.23(1H,td,J=4.8, 13.9), 2.42(1H,m), 2.55(1H,dd,J=13.9,4.0), 2.58(1H,dd,J=8.4,7.3), 2.78(1H,dd,J=14.3,8.4), 2.84(1H,m), 4.15(1H, d,J=8.4), 5.29(1H,dd,J=8.4,4.0), 5.69(1H,d,J=9.9), 5.71(1H,br s), 5.83(1H.d,J=15.0), 5.97(1H,d,J=9.9), 6.10(1H,m), 6.13(1H,d,J=12.8), 6.20(1H,d,J=11.0), 6.63(1H,dd,J=15.0,11.0), 6.92(1H.d,J=15.0), 7.89(1H,dd,J=15.0,12.1)

Figure 8:
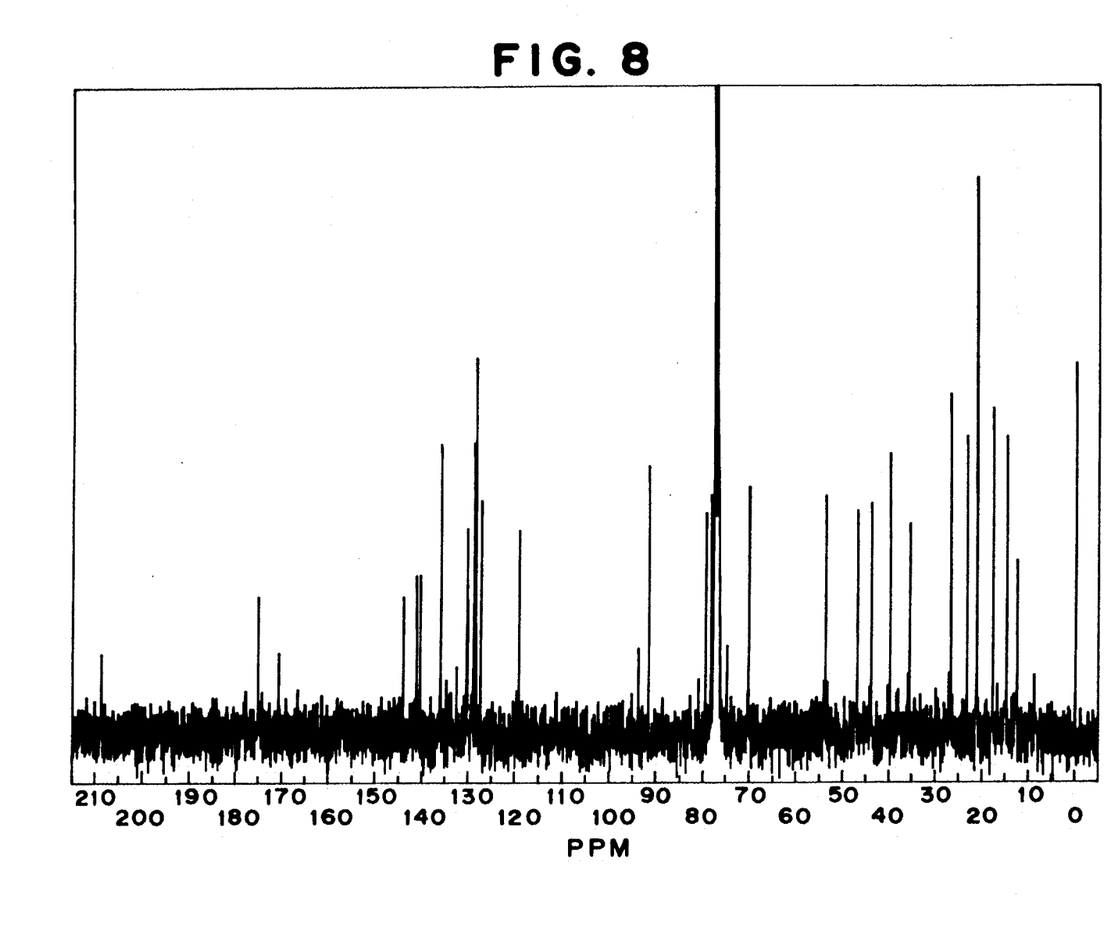
FIG. 8 shows the 100 MHz $^{13}$C NMR spectrum of the antibiotic Mer-AF1032B measured in CDCl$_3$.

(12) $^{13}$C-NMR Spectrum: as shown in FIG. 8 (measured in CDCl$_3$ and the data relating to the multiplicity of the signals were obtained by DEPT experiment): δ TMS(ppm): 208.7s, 175.2s, 170.6s, 143.8s, 141.1d 140.1s, 135.8d, 130.4d, 130.1s, 129.0d, 128.9d, 128.2d, 128.2d, 127.2d, 118.9d,91. 7d, 79.4d, 78.2s, 70.1d, 53.7s, 46.9t, 44.0d, 40.0d, 35.4t, 27.0d, 23.2q, 20.9q, 20.9q, 17.6q, 14.8q, 12.3q; and (13) Classification by neutral, acidic, or basic property: weakly acidic, on a silica gel thin layer plate with a pH indicator.

The antibiotics Mer-AF1032A and Mer-AF1032B were isolated from the culture product obtained by cultivating the strain AF1032 belonging to genus Penicillium which was isolated from soil collected in Hadano City, Kanagawa Prefecture, Japan. This strain is one example of the strains that can be most effectively utilized in the present invention.

This strain exhibits the following microbial characteristics:

1. Cultural characteristics: All cultivations were carried out at 26° C. and cultural characteristics on agar plates were observed.

(1) Czapek's solution agar

Colonies on Czapek's solution agar are rather slow, 26 mm in diameter after cultivation for two weeks. The surface of the colony is velvety white and radiating waves are formed during growth. No exudates are formed. Conidia cannot be observed in usual culture. However, conidia are observed after a prolonged cultivation. Soluble pigments are formed into the medium, and the colony color of reverse side is yellowish gray.

(2) Malt extract agar

Colonies on malt extract agar are rather slow, 25 mm in diameter after cultivation for two weeks. The surface of the colony is velvety with growth of convex hyphae to a height of 3–5 mm. The colony color at the center is bright gray. No exudates are formed and abundant conidia are formed at the gray growing portion of the colony. No pigment sinks into the medium, and the colony color of reverse side is yellowish brown.

2. Morphological characteristics

The colonies on malt extract agar, conidiophores develop from aerial hyphae. The conidiophores are short, 7.0–20 μm×1.8–2.0 μm, and have smooth surfaces. Although vesicles are not formed, the tips of the conidiosphores are slightly swollen. A single penicillus forms at the top of the conidiophore. Five to eight ampule-shaped sterigmata (6.0–8.5μm×2.0–2.5μm) form and some taper toward the tips. Spherical and semi-spherical conidia measuring 1.8 μm to 3.0 μm in diameter are formed to the top of sterigmata and many tubercules are observed on the surface of the conidia. The head of the conidial chains are formed in a random pattern.

From the foregoing microbial characteristics, it was concluded that this strain is a kind of fungi and belongs to the genus Penicillium. The morphological characteristics of the strain were compared with those of strains listed in Genus Penicillium (J. I. Pitt, 1979), but the strain could not be identified. It was therefore named Penicillium sp. Mer-AF1032.

The inventors deposited this strain as Penicillium sp. Mer-AF1032 at the Fermentation Research Institute, Agency of Industrial Science and Technology (1-1-3, Higashi Tsukuba, Ibaraki 305, Japan) under the access number FERM P-12157.

The antibiotics Mer-AF1032A and Mer-AF1032B can be prepared by inoculating the above-described strain into a medium containing assimilable nutrients, and cultivating the medium under an aerial condition. The strains producing the antibiotics Mer-AF1032A and Mer-AF1032B are not limited to the strain described above, and any strain can be used in the present invention so far as it belongs to genus Penicillium and is able to produce the antibiotics Mer-AF1032A and Mer-AF1032B. The salts of these antibiotics fall within the scope of the present invention and can be prepared by converting Mer-AF1032A and Mer-AF1032B obtained by the cultivation by a method well known to persons of ordinary skill in the art.

The cultivation process of the above-described microorganism can be conducted basically according to the cultivation methods generally used for microorganisms. For the production of Mer-AF1032A and Mer-AF1032B, aerobic cultivation, preferably submerged aerobic cultivation, may be used.

Any known nutrients used for the cultivation of genus Penicillium may be utilized in the medium. Any type of medium such as a synthetic medium, a semi-synthetic medium, or a natural medium may be used. As the source of carbon, the medium may contain glucose, sucrose, fructose, glycerol, dextrin, starch, molasses, corn steep liquor, organic acids, or mixtures thereof. Examples of the source of nitrogen include organic nitrogen sources such as pharmamedia, peptone, meat extract, yeast extract, soybean meal, casein, amino acids, and urea; and inorganic nitrogen sources such as sodium nitrate and ammonium sulfate, which may be used alone or in combination. If desired, sodium salts, potassium salts, magnesium salts, phosphates, or other heavy metal salts may be added. Furthermore, where significant foaming occurs during the cultivation, various kinds of known defoaming agents may suitably be added to the medium. However, the amount added should be kept within the range that does not affect the production of the desired compound. For example, the defoaming agent should preferably be used at a concentration of not more than 0.05%.

The pH of the culture medium is preferably within the optimum pH range for the strain used, which is generally around neutral. The temperature of the medium should be within the range that is suitable for good growth of the strain used, which is generally between 20° and 40° C. and most preferably about 30° C. The cultivation period should generally be about one to five days, preferably about 88 hours. It will be understood that the conditions for the cultivation herein described may be suitably altered depending on the type or characteristics of the microorganism used or other outside conditions, and that the optimum conditions can be selected or controlled within the above-described conditions.

The antibiotics Mer-AF1032A and Mer-AF1032B accumulated in the cultivation medium can be separated after the cultivation by removing the mycelia using a known separation method such as, for example, filtration, centrifugation, or extraction, and recovering the antibiotics from the resulting filtrate, supernatant, extract, or the like.

Separation and purification can be conducted according to known methods. Examples of the separation and purification process include extraction using a solvent such as ethyl acetate or n-butanol; adsorption on activated charcoal or on a resin such as Amberlite XAD (Rohm and Haas) or Diaion HP-20 (Mitsubishi Kasei) and elution using methanol-water or acetone-water; gel-filtration using Sephadex LH-20 (Pharmacia) or Bio-Gel P-2 (Bio-Rad); column chromatography or thin layer chromatography using silica gel or alumina; or preparative high-performance liquid chromatography (preparative HPLC) using a normal or reverse column. These processes can be used singly, in suitable combination, or repeatedly, if desired, for separation and purification.

Table 1 shows the antibacterial spectrum of the antibiotics Mer-AF1032A and Mer-AF1032B obtained by the liquid medium dilution method against various microorganisms.

TABLE 1

| Microorganism | Minimum inhibitory concentration (μg/ml) Mer-AF1032A | Mer-AF1032B |
|---|---|---|
| Candida albicans 5-305 | 3.13 | 6.25 |
| Candida albicans 40009 | 3.13 | 6.25 |
| Candida albicans DCU1001 | 3.13 | 6.25 |
| Candida albicans 3147 | 3.13 | 6.25 |
| Saccharomyces cerevisiae | >100 | >100 |
| Aspergillus fumigatus IFM41088 | 50 | >100 |
| Aspergillus fumigatus IFM4942 | 50 | >100 |
| Staphylococcus aureus 209P | >100 | >100 |
| Bacillus subtilis ATCC6633 | 100 | >100 |
| Escherichia coli K-12 | >100 | >100 |

Cultivation medium: fungi: YNBG, pH 6.4; bacteria: Mueller-Hinton, pH 7.0.
Cultivation temperature: 35° C.
Evaluation: fungi and bacteria were visibly observed after 40 and 20 hours, respectively.

From the results described above, it is apparent that the antibiotics Mer-AF1032A and Mer-AF1032B have antibacterial activity against *Candida albicans* and *Aspergillus fumigatus*.

EXAMPLES

The present invention will be further illustrated by the following Examples, by which the scope of the present invention is not be limited. Of the mediums described, all percentages (%) quoted in the medium are based on weight/volume percent unless otherwise specifically mentioned.

EXAMPLE 1

A loopful of the slant culture of strain AF1032 (potatodextrose agar medium) was inoculated into 100 ml of inoculum medium (2% potato starch; 1% glucose; 2% soybean meal; 0.1% potassium dihydrogenphosphate; 0.05% magnesium sulfate, pH not adjusted) contained in a 500 ml Erlenmeyer flask, and cultured for three days at 28° C. on a rotary-shaking incubator to prepare a first-stage inoculum. The first-stage inoculm (300 ml) was inoculated into 5 liters of production medium consisting of the same ingredients as those described above contained in a 10 liter jar fermentor, and then the medium was cultured at 28° C. for 88 hours with aeration and stirring (aeration of 5L/min., and stirring at 300 r.p.m.). After the cultivation, the cultured medium (about 10 liters) was centrifuged to separate mycelia and about 8 liters of cultural supernatant was obtained. The supernatant was adjusted to pH 3 with 5N HCl and was extracted with 8 liters of ethyl acetate. The ethyl acetate extract was washed with 8 liters of saturated aqueous sodium chloride, dried over anhydrous sodium sulfate, and then concentrated and dried under a reduced pressure to give 7.2 g of solid. The solid was dissolved in 50 ml of chloroform and adsorbed on silica gel which had previously been packed into a column using chloroform (Wako gel C-300, 3φ×47 cm). After being washed with 100 ml of chloroform, the column was subjected to development using a mixture of chloroform and methanol (20:1) and the eluent was fractionized into 10 ml fraction. The antibiotics Mer-AF1032A and Mer-AF1032B were detected by the measurement of antibacterial activity of the individual fractions according to the paper-disk method (microorganism used: *Candida albicans*) and by thin layer chromatography (Merck, Art. 5714, colored by vanillin-phosphoric acid) using a mixture of chloroform and methanol (10:1) as a developer. Active fractions were collected, concentrated and dried under a reduced pressure. The resulting dried residue was dissolved in 30 ml of a mixture of toluene, ethyl acetate, and acetic acid (50:30:1) and was further subjected to silica gel column chromatography, i.e., the solution was applied on a silica gel column (Merck, Art. 7734, 3φ×47 cm) which had previously been packed using a developer composed of the same components, and the column was developed using 800 ml of the developer composed of the same components to obtain 10 ml of fractions. The antibiotics Mer-AF1032A and Mer-AF1032B were detected in the same manner as described above. Active fractions exhibiting single spot on silica gel thin layer chromatography were collected. The active fraction was concentrated to 100 ml under a reduced pressure, washed with 100 ml of 5% aqueous sodium hydrogen carbonate, and then concentrated and dried under a reduced pressure to give 240 mg of crude product. The residue was dissolved in 3 ml of methanol and applied on a Sephadex LH-20 column (Pharmacia, 2.2φ×50 cm) which had previously been packed using methanol. The column was developed by methanol and the effluent was fractionized into 5 ml of fractions. The antibiotics Mer-AF1032A and Mer-AF1032B were detected by antibacterial activity and silica gel thin layer chromatography, and the fractions that exhibited single spot on the silica gel thin layer chromatography were collected. Further purification was carried out using preparative HPLC, i.e., after methanol was removed under a reduced pressure, the residue was dissolved in 5 ml of 70% (v/v) methanol/0.05M acetic acid-aqueous triethylamine solution (pH 6.5) and applied on a preparative HPLC under the following conditions: column: YMC-Pack S-343 I-15 ODS, 2φ×25 cm; mobil phase: 74% (v/v) methanol/0.05M acetic acid-aqueous triethylamine solution (pH 6.5); flow rate: 7.0 ml/min.; and detection: UV 340 nm. Two antibiotics Mer-AF1032A and Mer-AF1032B were separately fractionated which exhibited the retention time of 23.0 min. and 31.6 min., respectively. After being removed of methanol under a reduced pressure, the fractions obtained were lyophilized to give 50 mg and 34 mg of the antibiotics Mer-AF1032A and Mer-AF1032B, respectively.

The antibiotics Mer-AF1032A and Mer-AF1032B or their pharmacologically acceptable salts may be formulated in a pharmaceutical composition in the form of, for example, tablet, powder, capsule, injection, inhalant, or external preparation by ordinary methods, and may be administered orally or parenterally as a clinically useful antifungal agent. The dose may be varied depending on the condition of the patient or the route of administration. For example, the daily dose for an adult patient is 10 to 1000 mg, preferably 200 to 600 mg.

The antibiotics Mer-AF1032A and Mer-AF1032B of the present invention exhibit antifungal activity, and their physicochemical properties show that they are characterized by novel structures distinct from those of the known antifungal substances. On the basis of these properties, the antibiotics Mer-AF1032A and Mer-AF1032B of the present invention are understood to be useful for medicaments, pesticides, or materials for preparation thereof. One of ordinary skill in the art will recognize that improvements and modifications may be made while remaining within the scope and spirit of the present invention. The scope of the present invention is determined solely by the appended claims.

What is claimed is:

1. Antibiotic Mer-AF1032A represented by the following formula (I):

2. Antibiotic Mer-AF1032B represented by the following formula (II):

3. A pharmaceutical composition comprising an effective amount of an antibiotic selected from the group consisting of Mer-AF1032A represented by the following formula (I):

and Mer-AF1032B represented by the following formula (II):

together with a pharmaceutically-acceptable carrier or coating.

* * * * *